United States Patent [19]

Chang et al.

[11] Patent Number: 4,578,521
[45] Date of Patent: Mar. 25, 1986

[54] SHAPE-SELECTIVE CATALYTIC OXIDATION OF PHENOL

[75] Inventors: Clarence D. Chang, Princeton; Stuart D. Hellring, Plainsboro, both of N.J.

[73] Assignee: Mobil Oil Corporation, New York, N.Y.

[21] Appl. No.: 697,804

[22] Filed: Feb. 4, 1985

[51] Int. Cl.4 .................. C07C 39/08; C07C 37/60
[52] U.S. Cl. ................................ 568/771; 568/803
[58] Field of Search ........................... 568/771, 803

[56] References Cited

U.S. PATENT DOCUMENTS

| 3,580,956 | 5/1971 | Bloch | 568/771 |
|---|---|---|---|
| 3,914,324 | 10/1975 | Maggioni | 568/771 |
| 4,301,307 | 11/1981 | Jouffret | 568/771 |
| 4,396,783 | 8/1983 | Esposito et al. | 568/771 |

Primary Examiner—Werren B. Lone
Attorney, Agent, or Firm—Alexander J. McKillop; Michael G. Gilman; James F. Powers, Jr.

[57] ABSTRACT

This invention provides a process in which phenol is reacted with hydrogen peroxide to form hydroquinone in the presence of a shape-selective zeolite catalyst such as HZSM-5. Essentially no catechol byproduct is produced.

14 Claims, No Drawings

SHAPE-SELECTIVE CATALYTIC OXIDATION OF PHENOL

BACKGROUND OF THE INVENTION

Dihydroxybenzene compounds have found wide application in industrial processes. Hydroquinone functions as a reducing agent in chemical reactions, and as an antioxidant in gasoline, rubber, plastics, and the like. Hydroquinone is useful in photographic chemistry, and hydroquinone derivatives are utilized as food antioxidants.

Ind. Eng. Chem. Prod. Res. Dev., 15, 212 (1976) by J. Varagnal describes several known processes for producing hydroquinone: (1) aniline is oxidized by magnesium dioxide to benzoquinone, which then is catalytically reduced to hydroquinone; (2) p-diisopropylbenzene is air-oxidized to a dihydroperoxide, which by acidic cleavage yields hydroquinone and acetone; (3) high pressure and temperature carbonylation of acetylene yields hydroquinone directly; and (4) benzene is electrochemically oxidized to benzoquinone which in turn is reduced electrochemically.

Of particular interest with respect to the present invention are processes in which aromatic compounds are hydroxylated with hydrogen peroxide in the presence of a catalyst.

U.S. Pat. No. 3,580,956 describes a process for nuclear hydroxylation of a substituted benzene or naphthalene compound which involves reacting the compound with hydrogen peroxide in contact with a faujasite or mordenite aluminosilicate catalyst. Phenol is converted into a mixture of dihydroxybenzenes and tar byproduct.

U.S. Pat. No. 3,914,324 describes a process in which phenol is hydroxylated with hydrogen peroxide in the presence of an alkanoic acid and an acid catalyst such as phosphoric acid or trichloracetic acid. The process yields a mixture of catechol and hydroquinone.

U.S. Pat. No. 4,301,307 describes a process for hydroxylation of aromatic compounds which involves reacting an aromatic compound with hydrogen peroxide in the presence of trifluoromethanesulfonic acid catalyst. Phenol is hydroxylated to a hydroquinone/catechol mixture with a 2:1 molar selectivity.

U.S. Pat. No. 4,396,783 describes a process for hydroxylating aromatic hydrocarbons which involves reacting an aromatic compound with hydrogen peroxide in the presence of a synthetic zeolitic catalyst such as titanium silicalite. Phenol is converted to an approximately equimolar mixture of hydroquinone and catechol, with an additional yield of tar byproduct.

There is continuing interest in the development of new and improved processes for selective oxidation of aromatic compounds.

Accordingly, it is an object of this invention to provide an improved process for selective hydroxylation of substituted aromatic compounds.

It is another object of this invention to provide a process for selective hydroxylation of phenol to hydroquinone.

It is a further object of this invention to provide a process for shape-selective hydroxylation of phenol to hydroquinone with hydrogen peroxide in the presence of a heterogeneous catalyst.

Other objects and advantages of the present invention shall become apparent from the accompanying description and examples.

DESCRIPTION OF THE INVENTION

One or more objects of the present invention are accomplished by the provision of a process embodiment for shape-selective oxidation of phenol which comprises reacting phenol with hydrogen peroxide at a temperature between about 20°–150° C. in the presence of a zeolite catalyst having a Constraint Index between about 1–12 and an Alpha value greater than about 20, and producing hydroquinone product.

In a further embodiment, this invention provides a process for shape-selective hydroxylation of phenol which comprises adding hydrogen peroxide by gradual addition to a reaction medium which is at a temperature between about 20°–150° C. and which comprises phenol and a zeolite catalyst having a Constraint Index between about 8–10, a silica/alumina ratio between about 12–500 and an Alpha value between about 50–500, and producing a dihydroxybenzene product consisting essentially of 1,4-dihydroxybenzene.

The hydrogen peroxide is employed as an aqueous solution in a concentration between about 3–90 weight percent of hydrogen peroxide, and preferably in a concentration between 30–90 weight percent.

The phenol and the hydrogen peroxide are employed in a molar ratio between about 2–20:1 of phenol to hydrogen peroxide.

Optimal results are achieved if the hydrogen peroxide is added gradually at a slow rate to a reaction medium containing phenol and zeolite catalyst. A typical period of hydrogen peroxide addition is between about 0.1–2 hours.

The molar excess of phenol functions as a reactive medium during the course of the phenol hydroxylation. Optionally, an organic solvent can be included in the reaction. Suitable organic media include water-miscible organic solvents such as acetone, tetrahydrofuran, methanol, acetic acid, and the like, which function as a diluent in the reaction medium.

As an alternative procedure, a water-immiscible solvent can be employed, so that the reaction medium consists of two liquid phases and a solid zeolite catalyst phase. Under these conditions, all of the hydrogen peroxide can be charged at the beginning of the reaction period. The reaction rate is moderated by the controlled exchange of phenol and hydrogen peroxide between the two immiscible liquid phases.

A solvent component usually is employed in a quantity between about 0.1–10 moles per mole of phenol and hydrogen peroxide reactants.

An important objective in the practice of the invention process is to achieve the production of hydroquinone, without further oxidation of the hydroquinone to benzoquinone and degradation byproducts.

The use of a molar excess of phenol and/or an organic solvent and/or slow addition of hydrogen peroxide are factors which are adapted to control the oxidation environment in the reaction medium and enhance the yield of the hydroquinone primary oxidation product. Preferably, the effective concentration of hydrogen peroxide is maintained in the range between about 5–20 weight percent with respect to phenol in the oxidation environment of the reaction medium.

The reaction medium preferably is maintained at a temperature between about −25°–150° C., and the total period of the oxidation reaction is between about 0.5-4 hours, and typically the reaction time will be 1-2 hours. The reaction preferably is conducted under atmospheric pressure.

An essential aspect of the invention process is the presence of a specific type of zeolite catalyst composition in the reaction medium. The zeolite catalyst provides a shape-selective constrained access to and egress from the intracrystalline free space by virtue of having an effective pore size. The phenol and hydrogen peroxide interact within the pore structure of the zeolite catalyst, and shape-selective hydroxylation of phenol to hydroquinone occurs. The zeolitic intracrystalline constraints prevent the formation of catechol (1,2-dihydroxybenzene).

The shape-selective activity of the zeolite catalyst composition relates to a specific property of the crystalline zeolitic structure, i.e., the Constraint Index.

As described in U.S. Pat. No. 4,284,529 (incorporated by reference), a simple determination of the "Constraint Index" is accomplished by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 40° C. for at least 15 minutes. The zeolite is then flushed with helium and the temperature is adjusted between 290° C. and 510° C. to give an overall conversion of 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is analyzed, e.g., by gas chromatography, to determine the fraction remaining unchanged for each of the two hydrocarbons.

The Constraint Index is calculated as follows:

$$\text{Constraint Index} = \frac{\log (\text{fraction of hexane remaining})}{\log (\text{fraction of 3-methylpentane remaining})}$$

The Constraint Index approximates the ratio of the cracking rate constants for the two hydrocarbons. Zeolites suitable for the present invention process are those having a Constraint Index of 1-12. Constraint Index (C.I) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon | 0.4 |
| REY | 0.4 |
| Amorphous Silica-Alumina | 0.6 |
| Erionite | 38 |

The zeolite catalyst compositions which are unique in terms of shape-selective activity are those which have a Constraint Index between about 8-10, i.e., ZSM-5, ZSM-11 and ZSM-23 in the above list of catalyst species.

ZSM-5 is described in U.S. Pat. Nos. 3,702,886 and Re. 29,948, incorporated by reference.

ZSM-11 is described in U.S. Pat. No. 3,709,979, incorporated by reference.

ZSM-23 is described in U.S. Pat. No. 4,076,842, incorporated by reference.

Other suitable zeolites described in the patent literature include ZSM-12 (U.S. Pat. No. 3,832,449), ZSM-35 (U.S. Pat. No. 4,016,245), ZSM-38 (U.S. Pat. No. 4,046,859), and ZSM-48 (U.S. Pat. No. 4,375,573), incorporated by reference. These zeolites have a Constraint Index in the range between about 2-5. As determined by shape-selective activity, generally the preferred zeolite catalysts are those having a Constraint Index between about 2-10.

In addition to Constraint Index, the zeolite catalyst composition utilized in the invention process is characterized by another important property, i.e., the zeolite has an Alpha value greater than about 20, preferably about 50-500. The Alpha value is a measure of the acidity of a zeolite catalyst composition.

As disclosed in U.S. Pat. No. 4,351,979, the controlled acid activity of the zeolite catalyst is conveniently defined by the "Alpha" scale described in an article published in Journal of Catalysis, Vol. VI, pp 278-287(1966) which publication is incorporated herein by reference. In this test, the zeolite catalyst is contacted with hexane under prescribed conditions and the amount of hexane which is cracked is measured. From this measurement is computed the "Alpha" value used herein. For purposes of the present invention, all measurements of "Alpha" are at 538° C.

The zeolite catalyst compositions are synthesized in accordance with the procedures described in the above recited United States patents that are incorporated by reference.

To achieve the Alpha value acidity required for a present invention zeolite catalyst composition, the zeolite is converted from its as synthesized alkali metal form to the hydrogen form, generally by intermediate formation of the ammonium form as a result of ammonium ion exchange, and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB-VIII of the Periodic Table, such as nickel, zinc or rare earth metals. Prior to use the zeolite is calcined in an inert atmosphere, e.g., helium, or in an oxygen-containing atmosphere, e.g., air. Calcination is conducted at a temperature in the range of about 300°-700° C., and preferably between about 450°-550° C.

If a metal such as iron, palladium or platinum is ion-exchanged into the zeolite catalyst composition to function as a promoter for the oxidation reaction, the metal is incorporated in a quantity between about 0.05-10 weight percent, based on the zeolite catalyst weight.

The zeolite catalyst composition is employed in the invention process in a quantity between about 0.5-50 weight percent, based on the weight of phenol in the reaction medium.

After the completion of the oxidation reaction period, the hydroquinone product and unreacted phenol are recovered by conventional procedures, such as fractional distillation.

In the practice of the invention process, typically about 20–40 percent of the phenol is oxidized, and the selectivity to hydroquinone product is at least about 90 percent. The selectivity to dihydroxybenzenes essentially is 100 percent hydroquinone. Under optimal conditions, less than one percent catechol is produced, based on the total yield of dihydroxybenzene product.

The following examples are further illustrative of the present invention. The components and specific ingredients are presented as being typical, and various modifications can be derived in view of the foregoing disclosure within the scope of the invention.

EXAMPLE I

This Example illustrates the preparation of HZSM-5 zeolite catalyst compositions.

The following materials are employed:

Silicate Solution 42.2 lb. Q-Brand Sodium Silicate ($Na_2O/SiO_2=3.3$)
52.8 lb. Water

Acid Solution 612 grams Aluminum Sulfate
1600 grams Sulfuric Acid
7190 grams Sodium Chloride
72.2 Water

Organics 1290 grams Tri-n-propylamine
1110 grams n-Propylbromide

The silicate solution and acid solution are nozzle mixed to form a gelatinous precipitate that is charged to a 30 gallon stirred autoclave. When gelation is complete, the organics are added and the temperature raised to 155° C. with agitation. The reaction mixture is held at 155° C. with an agitation rate of 121 RPM for 17 hours. The product at this time is analyzed by X-ray diffraction to confirm the ZSM-5 structure.

The product is washed free of soluble salts and dried. The product has the following analysis:

$Al_2O_3$: 1.0
$SiO_2$: 74.4
$Na_2O$: 0.31
N: 2.26
C: 21.9

The ZSM-5 is precalcined in air at 370° C. and thereafter ammonium exchanged by contacting twice with 5N $NH_4Cl$ solution at 100° C. (15 ml per gram zeolite), then filtered, washed free of chloride and air dried.

The resulting ammonium form of ZSM-5 is converted to the hydrogen form by calcination in air at 1° C./minute to 538° C. and then held at 538° C. for 10 hours.

The HZSM-5 catalyst composition(I) is ball milled for two hours to form a fine powder. The fine powder is screened to the desired particle size range, e.g., 100–200 mesh.

A larger particle size range is obtained by pelleting the powder, and then crushing the pellets to a desired particle size range, e.g., 50–100 mesh.

A Cu-Zn/HZSM-5 catalyst composition is prepared by treating the above described HZSM-5 catalyst composition(I) with 0.1N $Cu(NO_3)_2$ solution twice at 80° C. for one hour each, using 5 ml of solution per gram of catalyst per ion-exchange cycle. The resultant composition is then ion-exchanged with 0.1N $Zn(NO_3)_2$. The washed and dried catalyst is slugged, crushed, and sized by screening. After calcination at 538° C. for three hours, the catalyst is found to contain 0.25% copper and 1% zinc by weight.

In a similar manner, the HZSM-5 catalyst composition(I) described above is impregnated with a calculated amount of $H_2PtCl_6$ solution to give 0.1% by weight of platinum in the final product. The resultant composition is calcined at 538° C. in air for 3 hours.

Other catalyst compositions are prepared in a similar manner by employing ZSM-11 and ZSM-23 zeolite substrates, respectively, instead of ZSM-5.

EXAMPLE II

This Example illustrates the shape-selective hydroxylation of phenol to hydroquinone in accordance with the invention process.

A reactor fitted with a stirrer, reflux condenser, thermometer and feeding funnel is charged with 100 grams of phenol and two grams of HZSM-5 catalyst composition (50–100 mesh). The reaction medium is heated to 80° C., and a 20 ml quantity of 40% $H_2O_2$ is added dropwise over a period of about one hour. The reaction is continued at 80° C. for another hour.

The product mixture is distilled under vacuum for recovery of hydroquinone product and unreacted phenol. About 70 grams of phenol and 27 grams of hydroquinone are recovered. The selectivity of phenol conversion to dihydroxybenzene product is about 99 percent hydroquinone and less than one percent catechol.

What is claimed is:

1. A process for shape-selective oxidation of phenol which comprises reacting phenol with hydrogen peroxide at a temperature between about 0°–150° C. in the presence of a zeolite catalyst having a Constraint Index between about 2–10 and an Alpha value greater than about 20, and producing hydroquinone product.

2. A process in accordance with claim 1 wherein the zeolite catalyst is ZSM-5.

3. A process in accordance with claim 1 wherein the zeolite catalyst is ZSM-11.

4. A process for shape-selective hydroxylation of phenol which comprises adding hydrogen peroxide by gradual addition to a reaction medium which is at a temperature between about 0°–150° C. and which comprises phenol and a zeolite catalyst having a Constraint Index between about 8–10, a silica/alumina ratio between about 12–500 and an Alpha value between about 50–500, and producing a dihydroxybenzene product comprising 1,4-dihydroxybenzene.

5. A process in accordance with claim 4 wherein the hydrogen peroxide is added as a 30–90 weight percent aqueous solution.

6. A process in accordance with claim 4 wherein the phenol and hydrogen peroxide are employed in a molar ratio between about 2–20:1 of phenol to hydrogen peroxide.

7. A process in accordance with claim 4 wherein the gradual addition of hydrogen peroxide to the reaction medium is over a period between about 0.1–2 hours.

8. A process in accordance with claim 4 wherein the reaction medium contains a water-miscible organic solvent diluent.

9. A process in accordance with claim 4 wherein the reaction medium contains a water-immiscible solvent phase.

10. A process in accordance with claim 4 wherein the zeolite catalyst is ZSM-5.

11. A process in accordance with claim 4 wherein the zeolite catalyst is ZSM-11.

12. A process in accordance with claim 4 wherein the zeolite catalyst contains ion-exchanged metal selected from Groups IB-VIII of the Periodic Table.

13. A process in accordance with claim 12 wherein the ion-exchanged metal is an oxidation promoter.

14. A process in accordance with claim 4 wherein the conversion selectivity of phenol to dihydroxybenzene product is essentially 100 percent to 1,4-dihydroxybenzene.

* * * * *